(12) United States Patent
Sakamoto et al.

(10) Patent No.: US 7,579,508 B2
(45) Date of Patent: *Aug. 25, 2009

(54) PROCESS FOR PRODUCING ALCOHOL

(75) Inventors: Toru Sakamoto, Wakayama (JP);
Osamu Tabata, Wakayama (JP);
Hideaki Ueoka, Ibaraki (JP)

(73) Assignee: Kao Corporation, Tokyo (JP)

( * ) Notice: Subject to any disclaimer, the term of this patent is extended or adjusted under 35 U.S.C. 154(b) by 184 days.

This patent is subject to a terminal disclaimer.

(21) Appl. No.: 10/570,899

(22) PCT Filed: Sep. 8, 2004

(86) PCT No.: PCT/JP2004/013383
§ 371 (c)(1),
(2), (4) Date: Mar. 7, 2006

(87) PCT Pub. No.: WO2005/026091
PCT Pub. Date: Mar. 24, 2005

(65) Prior Publication Data
US 2007/0032686 A1  Feb. 8, 2007

(30) Foreign Application Priority Data
Sep. 9, 2003 (JP) .............. 2003-316411

(51) Int. Cl.
*C07C 27/06* (2006.01)
(52) U.S. Cl. .......... 568/864; 568/861; 568/884; 568/885
(58) Field of Classification Search ............ 568/861, 568/864, 884, 885
See application file for complete search history.

(56) References Cited

U.S. PATENT DOCUMENTS

| | | | | |
|---|---|---|---|---|
| 2,094,127 A * | 9/1937 | Lazier | ............ | 568/840 |
| 2,109,844 A * | 3/1938 | Lazier | ............ | 568/885 |
| 2,241,417 A * | 5/1941 | Normann | ............ | 568/885 |
| 2,313,692 A * | 3/1943 | Baruch | ............ | 554/144 |
| 2,547,014 A * | 4/1951 | Kirby | ............ | 554/142 |
| 3,363,009 A * | 1/1968 | Schuman et al. | ............ | 568/864 |
| 4,179,454 A * | 12/1979 | Mehta et al. | ............ | 554/144 |
| 4,307,026 A * | 12/1981 | Kuiper | ............ | 554/145 |
| 4,346,240 A * | 8/1982 | Grey et al. | ............ | 568/842 |
| 4,696,911 A * | 9/1987 | Boerma et al. | ............ | 502/159 |
| 4,942,266 A * | 7/1990 | Fleckenstein et al. | ............ | 568/864 |
| 4,954,664 A | 9/1990 | Carduck et al. | | |
| 4,982,020 A * | 1/1991 | Carduck et al. | ............ | 568/864 |
| 5,118,448 A * | 6/1992 | Cooper | ............ | 554/168 |
| 5,233,100 A * | 8/1993 | Tabata et al. | ............ | 568/885 |
| 5,243,095 A * | 9/1993 | Roberts et al. | ............ | 568/864 |
| 5,364,986 A * | 11/1994 | Demmering et al. | ............ | 568/885 |
| 5,399,731 A * | 3/1995 | Wimmer | ............ | 554/167 |
| 5,399,792 A * | 3/1995 | Demmering | ............ | 568/864 |
| 5,406,004 A * | 4/1995 | Eastland et al. | ............ | 568/831 |
| 5,475,160 A * | 12/1995 | Singleton et al. | ............ | 568/864 |
| 5,478,789 A * | 12/1995 | Hattori et al. | ............ | 502/244 |
| 6,410,761 B1 * | 6/2002 | Saebo et al. | ............ | 554/126 |
| 6,610,868 B2 * | 8/2003 | Saebo et al. | ............ | 554/127 |
| 2006/0205965 A1 * | 9/2006 | Sakamoto et al. | ............ | 554/169 |
| 2007/0032686 A1 * | 2/2007 | Sakamoto et al. | ............ | 568/864 |

FOREIGN PATENT DOCUMENTS

| | | |
|---|---|---|
| DE | 1 668 219 | 3/1972 |
| JP | 63-39829 | 2/1988 |
| JP | 9-52853 | 2/1997 |
| JP | 2001-131102 | 5/2001 |

OTHER PUBLICATIONS

Sauer, Carboxylic Acids, Econimic Aspects, 2000, Kirk-Othmer Encyclopedia of Chemical Technology, pp. 0-7.*
U.S. Appl. No. 11/817,921, filed Sep. 6, 2007, Sakamoto, et al.

* cited by examiner

*Primary Examiner*—Porfirio Nazario-Gonzalez
*Assistant Examiner*—Yate' K Cutliff
(74) *Attorney, Agent, or Firm*—Oblon, Spivak, McClelland, Maier & Neustadt, P.C.

(57) ABSTRACT

The invention provides a process for producing an alcohol, including the step of hydrogenating a glyceride in the presence of a catalyst, adding water, or a process for producing an alcohol, including the step of hydrogenating a glyceride in the presence of a catalyst and in the presence of from 0.5 or more of water per mole of the starting glyceride.

18 Claims, No Drawings

PROCESS FOR PRODUCING ALCOHOL

FIELD OF THE INVENTION

The present invention relates to a process for producing an alcohol by catalytic hydrogenation reaction of a glyceride.

In the industrial production of a fatty alcohol, a process for producing a fatty alcohol by transesterificating glyceride with methanol, and then catalytically hydrogenating the resulting fatty ester of methanol is conventionally preferably used. Alternatively, a process of catalytically hydrogenating a wax ester obtained by esterifying a hydrolyzed fatty acid with a fatty alcohol is conventionally preferably used. A valuable glycerin product can be obtained this way at a high yield and at a high purity. The economical advantage of this 2-stage process is recognized.

On the other hand, the direct catalytic hydrogenation of glyceride enables an industrially important product such as a fatty alcohol to be directly obtained from naturally available fats and oils, but such a process is not generally used in industrial production. This is because a side reaction in which initially formed glycerin is hydrogenated on the surface of a catalyst occurs in the direct catalytic hydrogenation of glyceride, and thus glycerin cannot be obtained at a high yield.

From an economical viewpoint, the direct catalytic hydrogenation process cannot accordingly compete with the 2-stage process described above. This is also a reason that the process of directly hydrogenating triglycerides is not used on an industrial scale.

The method of obtaining a fatty alcohol by directly hydrogenating glyceride is described for example in U.S. Pat. No. 2,094,127, U.S. Pat. No. 2,109,844 or U.S. Pat. No. 2,241,417.

DE-A 1668219 describes a method of hydrogenating glyceride obtained from fats and oils.

Methods of directly hydrogenating glyceride are also described in U.S. Pat. No. 4,942,266, U.S. Pat. No. 4,954,664, U.S. Pat. No. 4,982,020, U.S. Pat. No. 5,364,986 or U.S. Pat. No. 5,475,160.

SUMMARY OF THE INVENTION

The present invention provides a process for producing an alcohol, including the step of hydrogenating a glyceride in the presence of a catalyst and added water.

In addition, the invention provides a process for producing an alcohol, comprising the step of hydrogenating a glyceride in the presence of a catalyst and 0.5 mole or more of water per mole of glyceride.

DETAILED DESCRIPTION OF THE INVENTION

The method described in U.S. Pat. No. 2,094,127, U.S. Pat. No. 2,109,844 or U.S. Pat. No. 2,241,417 is carried out at a reaction temperature of 200 to 400° C. at a hydrogen pressure of 100 to 300 bar to produce a fatty alcohol, but the desired reaction product glycerin is obtained only in a small amount and instead a large amount of propane, propanol or propylene glycol is obtained.

DE-A 1668219 describes a problem that a side reaction to produce propylene glycol, propanol or propane in place of the desired glycerin cannot be controlled.

In the methods described in U.S. Pat. No. 4,942,266, U.S. Pat. No. 4,954,664, U.S. Pat. No. 4,982,020, U.S. Pat. No. 5,364,986 and U.S. Pat. No. 5,475,160, the direct hydrogenation of glyceride to a fatty alcohol is conducted with a copper-based catalyst under relatively mild reaction conditions. 1,2-propanediol is produced at a high yield, and the process is not directed to the production of glycerin.

The present invention provides an economically extremely excellent process for producing an alcohol by the hydrogenation reaction of glyceride as a starting material in the presence of a catalyst, wherein, for example, glycerin having a high purity can be recovered.

The process for producing an alcohol according to the present invention is economically excellent and industrially extremely advantageous because, for example, decomposition of glycerin can be suppressed and glycerin having a high purity can be recovered.

In a preferred process of the present invention, the catalytic hydrogenation reaction of glyceride is carried out by adding water or in the co-presence of water. The amount of water is preferably 0.5 mole or more per mole of glyceride from the viewpoint of improvement of glycerin selectivity, more preferably 1 mole or more, even more preferably 2 moles or more, even more preferably 3 moles or more. With respect to energy consumption, the amount of water is preferably 10,000 moles or less per mole of glyceride, more preferably 5,000 moles or less, even more preferably 1,000 moles or less, even more preferably 500 moles or less.

The method of adding water or allowing water to be co-existent in the reaction is not particularly limited, and water may be added or be co-existent in either a gas or a liquid state. For example, there is a method wherein glyceride and water are previously mixed and fed to a reactor, a method wherein glyceride and water or water vapor are mixed before being fed to a reactor and then fed to the reactor, or a method wherein water or water vapor is added during the reaction.

Water formed by the reaction may be allowed to be co-existent during the hydrogenation reaction. The reaction to form water is hydrogenation, esterification, dehydration or condensation etc. For example a mixture of glyceride and a fatty acid may be fed to a reactor and water produced by hydrogenation of the fatty acid may be made to co-exist in the reactor. The amount of fatty acid is preferably from 0.5 to 10,000 moles per mole of glyceride from the viewpoint of the amount of water produced by the reaction, more preferably from 1 to 5,000 moles, even more preferably from 3 to 500 moles.

The fatty acid used is not limited in the invention, but includes preferably fatty acids derived from vegetable oils such as soy bean oil, rape seed oil, coconut oil, palm oil or palm kernel oil or animal oil such as beef tallow or fish oil. A mixture of fatty acids may be used.

Both water and a fatty acid may be added or made to co-exist in the hydrogenation reaction of glyceride.

In the present invention, the pressure in the catalytic hydrogenation reaction is preferably 1 to 50 MPa, more preferably 2 to 30 MPa. The temperature is preferably 120 to 300° C., more preferably 150 to 280° C.

The reactor used in the production process of the present invention is not particularly limited insofar as the catalytic hydrogenation reaction is feasible, and the reactor may be an ordinarily used device. Examples of the reactor include a fluidized bed reactor wherein catalytic hydrogenation reaction is carried out with a catalyst dispersed in fluid, a moving bed reactor wherein the catalytic hydrogenation reaction is carried out with fluid supplied while the entire catalyst layer drops gradually due to gravitational force, a fixed bed reactor wherein the catalytic hydrogenation reaction is carried out by supplying a fluid having a catalyst charged and immobilized therein, a multi-tube fixed bed reactor wherein the temperature of a catalyst layer can be isothermal, and a batch reactor wherein hydrogenation is carried out in a container charged with a catalyst, a starting material and water.

The glyceride used as a starting material in the present invention is not particularly limited, and known materials such as triglyceride, diglyceride and monoglyceride can be used. The triglyceride includes, for example, vegetable oils such as soybean oil, rapeseed oil, coconut oil, palm oil and palm kernel oil, animal oils such as tallow and fish oil, and synthetic triglyceride. The starting glycerides may be used singly or as a mixture of two or more thereof. As the glycerides, either those subjected to pretreatment such as a de-acid treatment or desulfurization treatment or those not subjected to any pretreatment may be used.

The catalyst used in the present invention may be a hydrogenation catalyst used in known alcohol production, and is not particularly limited. For example, a Cu-based catalyst such as Cu/Cr, Cu/Zn etc., Co-based catalyst such as Co/Mo, Co/Zr etc., and catalysts based on noble metals such as Re, Ru, Rh and platinum can be used. Among these catalysts, the Ru-based catalyst and Co-based catalyst are preferable, and further the Co-based catalyst, particularly the Co/Zr catalyst is more preferable.

The form of the catalyst is not particularly limited, and can be suitably selected from the forms of powder, granules, tablets, noodles, film, etc. When a catalyst precursor is used, the catalyst is obtained by reduction with a reducing substance. The reducing substance used here includes hydrogen, carbon monoxide, ammonia, hydrazine, formaldehyde and methanol, and these reducing substances may be used singly or as a mixture thereof and may be used in the presence of an inert gas such as nitrogen. When the catalyst precursor is reduced, either a gas phase reduction method or a liquid phase reduction method conducted in a hydrocarbon such as liquid paraffin or in a solvent such as dioxane, alcohol or ester may be used.

The alcohol obtained by the production process of the present invention is glycerin and a fatty alcohol derived from a fatty acid constituting the starting glyceride, and together with the fatty alcohol, glycerin can be recovered at a high yield.

The following examples further describe and demonstrate embodiments of the present invention. The examples are given solely for the purpose of illustration and are not to be construed as limitations of the present invention.

EXAMPLES

In Examples 1 to 4 and Comparative Examples 1 to 3, shown below, palm kernel oil (saponification value 244.8 mg KOH/g; water content 0.05% by weight; acid value 0.17 mg-KOH/g) subjected to de-acid treatment was used as the starting triglyceride.

Example 1

A commercial Co/Zr catalyst (G-67 manufactured by Süd-Chemie Inc.) was milled in a mortar and activated under the conditions of hydrogen pressure of 5 MPa, a temperature of 250° C, and 0.5 hour.

A 500-ml autoclave in a rotating stirring system was charged with 7.5 g of the commercial Co/Zr powdery catalyst subjected to the activation treatment, 150 g of starting triglyceride and 3 moles of water per mole of the starting glyceride. The mixture was heated to 230° C. and subjected to catalytic hydrogenation reaction for 3 hours under the conditions of a total pressure of 24.5 MPa and a stirring rate of 900 r/min.

Samples obtained during the reaction and after conclusion of the reaction were separated with water into an oil phase and aqueous phase, and the degree of conversion of triglyceride, the content of fatty alcohol in the oil phase and the glycerin selectivity were analyzed respectively by gas chromatography. The degree of conversion of triglyceride is defined by the following equation:

Degree of conversion of triglyceride (%)=(1−$TGt$/100)×100 wherein TGt is the amount (wt %) of triglyceride in the oil phase

The glycerin selectivity is defined as the ratio (wt %) of glycerin to the total organic material in the aqueous phase detected by gas chromatography. The material other than the fatty alcohol in the oil phase was mainly wax ester, monoglyceride and diglyceride, and the material other than glycerin in the aqueous phase was mainly propylene glycol, n-propanol and iso-propanol. The results after 3 hours of the reaction are shown in Table 1.

Example 2

After heating to 230° C., catalytic hydrogenation reaction was carried out for 5 hours under the conditions of a total pressure of 24.5 MPa and a stirring rate of 900 r/min in the same manner as in Example 1 except that the amount of added water was 20 moles per mole of the starting glyceride. The degree of conversion of triglyceride, the content of fatty alcohol in the oil phase and the glycerin selectivity after 3 and 5 hours of the reaction, respectively, were analyzed in the same manner as in Example 1. Results are shown in Table 1.

Example 3

After heating to 230° C., catalytic hydrogenation reaction was carried out for 7 hours under the conditions of a total pressure of 24.5 MPa and a stirring rate of 900-r/min in the same manner as in Example 1 except that the amount of added water was 50 moles per mole of the starting glyceride. The degree of conversion of triglyceride, the content of fatty alcohol in the oil phase and the glycerin selectivity after 6 and 7 hours of the reaction were analyzed in the same manner as in Example 1. Results are shown in Table 1.

Comparative Example 1

After heating to 230° C., catalytic hydrogenation reaction was carried out for 5 hours under the conditions of a total pressure of 24.5 MPa and a stirring rate of 900 r/min in the same manner as in Example 1 except that water was not added. The degree of conversion of triglyceride, the content of fatty alcohol in the oil phase and the glycerin selectivity after 5 hours of the reaction were analyzed in the same manner as in Example 1. Results are shown in Table 1.

Comparative Example 2

A commercial powdery Cu/Cr catalyst (KSC-1 manufactured by Nikki Chemical Co., Ltd.) was activated under the same conditions as in Example 1. A 500-ml autoclave in a rotating stirring system was charged with 3 g of the thus activated commercial Cu/Cr powdery catalyst and 200 g starting triglyceride, and the mixture was heated to 230° C. and subjected to catalytic hydrogenation reaction for 5 hours under the conditions of a total pressure of 24.5 MPa and a stirring rate of 900 r/min. The degree of conversion of triglyceride after 5 hours, the content of fatty alcohol in the oil phase and the glycerin selectivity after 5 hours of the reaction were analyzed in the same manner as in Example 1. Results are shown in Table 1.

TABLE 1

| | Reactiontime (hour) | Degree of convertion of triglyceride (%) | Content of fatty alcohol in oil phase (weight %) | Glycerine selectivity (%) |
|---|---|---|---|---|
| Example 1 | 3 | 99.3 | 31.1 | 61.5 |
| Example 2 | 3 | 98.0 | 46.1 | 81.6 |
| | 5 | 99.8 | 69.8 | 36.2 |
| Example 3 | 6 | 100 | 57.9 | 79.5 |
| | 7 | 100 | 63.8 | 57.3 |
| Comparative example 1 | 5 | 27.2 | 4.6 | <0.1 |
| Comparative example 2 | 5 | 99.8 | 62.7 | 0.4 |

Comparative Example 3

In a reactor having an inner diameter of 25 mm, equipped with a fixed bed filled with 300 cc of a commercially available Co/Zr catalyst (G-67 manufactured by Süd-Chemie Inc.), a catalytic hydrogenation was carried out at a pressure of 19.8 MPa, at a temperature of the catalyst bed of 230° C., at a hydrogen mole ratio of 75 to the starting oil and fat. The temperature of a heater provided in front of the reactor was 290° C. so that the temperature of the starting triglyceride and water in the catalyst bed was 230° C. The starting triglyceride was supplied to the reactor at a flow rate of 120 cc/h. At the outlet of the reactor, the conversion of triglyceride, the content of fatty alcohol in the oil phase and selectivity of glycerin were determined in the same way as Example 1. Results are shown in Table 2.

Example 4

According to the method of Comparative Example 3, the starting triglyceride at a flow rate of 60 cc/h and water in 50 moles per mole of glyceride were fed to a reactor, and the degree of conversion of triglyceride, the content of fatty alcohol in the oil phase and the glycerin selectivity at the outlet of the reactor were analyzed in the same manner as in Example 1. Results are shown in Table 2.

TABLE 2

| | Degree of convertion of triglyceride (%) | Content of fatty alcohol in oil phase (weight-%) | Glycerine selectivity (%) |
|---|---|---|---|
| Comparative example 3 | 74.1 | 40.0 | 1.0 |
| Example 4 | 97.0 | 44.8 | 48.3 |

Example 5

A 500-ml autoclave in a rotating stirring system was charged with a starting material (saponification value 247.3 mg-KOH/g; acid value 210.4 mg-KOH/g) including 0.75 g of triglyceride, 4.88 g of diglyceride and 6.38 g of monoglyceride in a palm kernel oil composition and 111.12 g of mixed fatty acids in a palm kernel oil composition, and water in 115 moles per mole of glyceride. The amount of water produced from the starting fatty acid by hydrogenation was calculated to be 16 moles per mole of the starting glyceride. For the reaction, 13 g of a commercial Co/Zr catalyst (G-67 manufactured by Süd-ChemieInc.) was used, and the mixture was heated to 230° C. and then subjected to catalytic hydrogenation reaction under the conditions of a total pressure of 24.5 MPa and a stirring rate of 900 r/min for 7 hours. The catalyst had been preliminarily activated under the conditions of a hydrogen pressure of 5 MPa, a temperature of 250° C. and 4 hours. The degree of conversion of glyceride is defined by the following equation:

The degree of conversion of glyceride (%)=(1−[glyceride]$_t$/[glyceride]$_0$)×100 wherein [glyceride]$_t$ is the sum (wt%) of triglyceride, diglyceride and monoglyceride in the oil phase after 7 hours of the reaction, and [glyceride]$_0$ is the sum (wt %) of triglyceride, diglyceride and monoglyceride in the starting material.

The glycerin selectivity was analyzed in the same manner as in Examples 1 to 4 and Comparative Examples 1 to 3. Results are shown in Table 3.

TABLE 3

| | Degree of convertion of triglyceride (%) | Content of fatty alcohol in oil phase (weight-%) | Glycerine selectivity (%) |
|---|---|---|---|
| Example 5 | 86.4 | 40.6 | 63.3 |

As can be seen from the results in Table 1, 2 and 3, glycerin was obtained at a high yield together with fatty alcohol in Examples 1 to 5. In Comparative Example 1, on the other hand, the degree of conversion of triglyceride was low, and the yield of fatty alcohol was low. The organic material in the aqueous phase was decomposed glycerin products, that is, propylene glycol, n-propanol and iso-propanol, and glycerin was not detected. In Comparative Example 2 and 3, the majority of the organic material in the aqueous phase was decomposed glyceride products, that is, propylene glycol, n-propanol and iso-propanol, and the glycerin selectivity was very low.

The invention claimed is:

1. A process for producing glycerin and an alcohol, comprising hydrogenating a glyceride in the presence of a catalyst and added water, thereby producing said glycerin and alcohol, wherein the alcohol is derived from the acid constituting the glyceride.

2. A process for producing glycerin and an alcohol, comprising hydrogenating a glyceride in the presence of a catalyst and 0.5 mole or more of water per mole of glyceride, thereby producing said glycerin and alcohol, wherein the alcohol is derived from the acid constituting the glyceride.

3. The process according to claim 2, wherein all or a part of the water is produced by a reaction other than said hydrogenating of said glyceride in the presence of said catalyst and said water.

4. The process according to claim 1 or 2, wherein the hydrogenating is conducted in the presence of a fatty acid.

5. The process according to claim 1 or 2, wherein the hydrogenating is conducted by adding a fatty acid.

6. The process according to claim 1 or 2, wherein the alcohol is a fatty alcohol.

7. The process according to claim 2, wherein the amount of water per mole of glyceride is 1 mole or more.

8. The process according to claim 2, wherein the amount of water per mole of glyceride is 2 moles or more.

9. The process according to claim 2, wherein the amount of water per mole of glyceride is 3 moles or more.

10. The process. according to claim 1 or 2, wherein the glyceride comprises a triglyceride.

11. The process. according to claim 10, wherein the triglyceride is derived from palm kernel oil.

12. The process according to claim 1, wherein the amount of water per mole of glyceride is 1 mole or more.

13. The process according to claim 1, wherein the amount of water per mole of glyceride is 2 moles or more.

14. The process according to claim 1, wherein the amount of water per mole of glyceride is 3 moles or more.

15. The process according to claim 1 or 2, wherein the hydrogenating is carried out at a pressure of 1 to 50 MPa.

16. The process according to claim 1 or 2, wherein the hydrogenating is carried out at a pressure of 2 to 30 MPa.

17. The process according to claim 1 or 2, wherein the hydrogenating is carried out at a temperature of 120 to 300° C.

18. The process according to claim 1 or 2, wherein the hydrogenating is carried out at a temperature of 150 to 280° C.

* * * * *